(12) United States Patent
Nyberg

(10) Patent No.: US 10,893,974 B2
(45) Date of Patent: *Jan. 19, 2021

(54) BASE PLATE OF AN OSTOMY APPLIANCE

(71) Applicant: Coloplast A/S, Humlebaek (DK)

(72) Inventor: René Ferm Nyberg, Skovlunde (DK)

(73) Assignee: Coloplast A/S, Humlebaek (DK)

( * ) Notice: Subject to any disclaimer, the term of this patent is extended or adjusted under 35 U.S.C. 154(b) by 350 days.

This patent is subject to a terminal disclaimer.

(21) Appl. No.: 15/952,257

(22) Filed: Apr. 13, 2018

(65) Prior Publication Data

US 2018/0228641 A1    Aug. 16, 2018

Related U.S. Application Data

(63) Continuation of application No. 14/649,217, filed as application No. PCT/DK2013/050412 on Dec. 5, 2013, now Pat. No. 9,968,480.

(30) Foreign Application Priority Data

Dec. 6, 2012    (DK) .................................. 2012 70765

(51) Int. Cl.
    *A61F 5/445*    (2006.01)
    *A61F 5/443*    (2006.01)
    *A61F 5/448*    (2006.01)

(52) U.S. Cl.
    CPC .............. *A61F 5/445* (2013.01); *A61F 5/443* (2013.01); *A61F 5/448* (2013.01); *A61F 2005/4483* (2013.01)

(58) Field of Classification Search
    CPC .......... A61F 5/443; A61F 5/445; A61F 5/448; A61F 2005/4483
    See application file for complete search history.

(56) References Cited

U.S. PATENT DOCUMENTS

| 4,834,731 | A | * | 5/1989 | Nowak | ................... | A61F 5/448 |
| | | | | | | 604/339 |
| 5,004,464 | A | * | 4/1991 | Leise, Jr. | ................ | A61F 5/445 |
| | | | | | | 604/338 |
| 5,125,917 | A | * | 6/1992 | Whealin | ................. | A61F 5/448 |
| | | | | | | 604/332 |
| 5,330,454 | A | * | 7/1994 | Klingler | .................. | A61F 5/448 |
| | | | | | | 604/338 |
| 5,607,413 | A | * | 3/1997 | Holmberg | ............... | A61F 5/448 |
| | | | | | | 604/332 |

(Continued)

*Primary Examiner* — Susan S Su
(74) *Attorney, Agent, or Firm* — Coloplast Corp., Coloplast A/S; Nick Baumann

(57) ABSTRACT

A base plate of an ostomy appliance includes a film, an adhesive disposed on a proximal surface of the film, an annular ring connected to the distal surface of the film, and a release liner removably attached to the adhesive. A stoma-receiving through-going hole is formed through the film and the adhesive and the release liner. A first section of the base plate extends radially from the stoma-receiving through-going hole to a second section of the base plate, and the second section extends radially from the first section to an outermost perimeter edge of the base plate. The base plate is formed to have a heat-set curvature such that a proximal side of the second section is convex and a distal side of the second section is concave relative to the annular ring.

16 Claims, 4 Drawing Sheets

(56) References Cited

U.S. PATENT DOCUMENTS

| | | | |
|---|---|---|---|
| 2002/0088080 A1* | 7/2002 | Fenton | A61F 5/445 15/389 |
| 2003/0088219 A1* | 5/2003 | Metz | A61F 5/448 604/339 |
| 2005/0054997 A1* | 3/2005 | Buglino | A61F 5/443 604/332 |
| 2011/0218507 A1* | 9/2011 | Andersen | A61F 5/445 604/338 |
| 2013/0096523 A1* | 4/2013 | Chang | A61L 28/0015 604/344 |

* cited by examiner

BASE PLATE OF AN OSTOMY APPLIANCE

The invention relates to an adaptable ostomy base plate. In particular, the invention relates to an adaptable ostomy base plate for ostomies or stomas located on a bulge or hernia on the skin surface of a user.

BACKGROUND

In connection with surgery for a number of diseases in the gastro-intestinal tract, one of the consequences in many cases is that the patient is left with an abdominal stoma, such as a colostomy, an ileostomy or a urostomy in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time.

An ostomy appliance may be in the form of a one-piece appliance for which a collecting bag for human body wastes is permanently, or fixedly, secured to an adhesive base plate for attachment to the human skin. Alternatively, the ostomy appliance may be a two-piece appliance comprising a base plate and a collecting bag which may be coupled to and uncoupled from each other through a coupling means. This has the effect that the base plate does not need to be separated from the skin of the user as often as exchange of the collecting bag requires. The base plate may need only to be changed every third or fourth day depending on the user, whereas the collecting bag may be changed more than once per day. Typically, it is desirable to need as few exchanges of the base plate as possible in order to reduce the risk of skin complications.

One of the main concerns of ostomates using ostomy appliances having an adhesive base plate for attachment to the skin surrounding a stoma, and where a collecting bag is attached to the base plate for collecting stoma output, is that the ostomy adhesive attachment may be compromised resulting in leakage or even complete detachment of the ostomy appliance.

Numerous attempts have been made to solve this problem and even though some attempts have been partly successful, still there exist no products which completely solve this problem.

One reason why this is so difficult to solve is the fact that stomas and peoples anatomy are very different. Different considerations need to be made for thin people than for larger people, for different skin types, for placement of the stoma which may vary a lot from person to person, for scar tissue surrounding the stoma, for local irregular skin topography and combinations of all of the above.

Particularly in relation to persons suffering from hernia, i.e. the phenomenon that a bodily structure (e.g. the intestine) protrudes through a rupture in smooth muscle tissue surrounding it, experience shows that it is often very difficult to attach an ostomy appliance to the skin surface where the hernia is located in a manner that provides satisfactory protection against leakage from stomal fluids. It is not uncommon that the surgical procedure undertaken to make a stoma on a patient also results in a weakening of the muscle tissue of the stomach wall which may consequently lead to the formation of a hernia where the stoma is located on the skin surface (or close or adjacent to the stoma).

In some cases where the stoma is located on a hernia, an additional complication may occur as gravity forces the protruding intestines downward and consequently also force the involved skin surface downward. Thereby, a stoma located on the hernia may begin to "point" downward (i.e. towards the user's feet) depriving the user of direct visual contact with the stoma and/or the peristomal skin surface. This is of course a great disadvantage for users applying their product themselves (which is the great majority of users) since the risk of misalignment or improper positioning of the product is largely increased. As a consequence, in such cases leakage problems may occur much more frequently.

Moreover, a hernia is not a static phenomenon. It is almost certain never to take a perfect geometrical shape but instead often has a highly irregular topography. This may be caused by many factors such as conditions in the physical surroundings of the user, level of activity of the user and contents of the bowels at any given time, just to mention a few.

In addition to the formation of hernias, other physical conditions or pathologies may also mean or lead to irregular skin topography such as bulges or otherwise "hilly" stomach skin surface, the causes including e.g. trauma and/or obesity.

DESCRIPTION OF RELATED ART

EP1178766 discloses a deformable pad for removably securing an ostomy bag to the skin of a patient consisting essentially of a plastics film bonded to an adhesive material; the pad having an opening for receiving stomal waste, the opening being surrounded by (i) a pliable convex formation of substantially uniform thickness on a bodyside face of the pad, or (ii) a hollow frustoconical ring of substantially uniform thickness extending outwardly from a bodyside face of the pad.

GB2311467 describes an ostomy appliance comprising a pouch and an adhesive flange coupled to the pouch for securing the appliance with respect to the skin of a wearer. The adhesive flange has an aperture which communicates with an interior of the pouch and comprises a plurality of fingers which extend away from the aperture. The document also describes an adhesive flange for an ostomy appliance.

SUMMARY OF THE INVENTION

The present invention provides a base plate to be used as part of or with an ostomy appliance. Particularly, the invention provides having one or more sections having a shape that can be adapted or physically altered from one shape to another in order to both assist the user in applying the base plate in an easier manner and to achieve a better fit to the body. The base plate is especially advantageous to be used on users suffering from and having their stoma located on a non-planar and non-regular skin surface.

DETAILED DESCRIPTION OF THE INVENTION

Figure 1A:
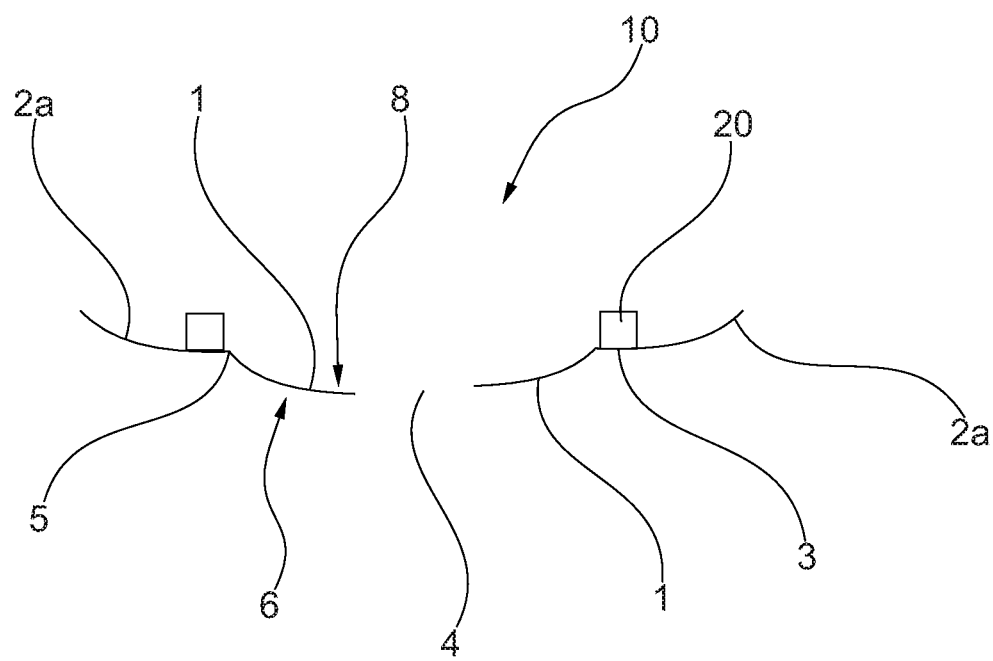
FIG. 1*a* is a schematic sectional view of an ostomy base plate according to embodiments of the invention.

For interpretations in the context of the present application, some definitions regarding the subject matter of the attached claims are presented below.

When referring to the proximal side of a device or part of a device, the referral is to the skin-facing side, when the ostomy appliance is worn by a user. Likewise whenever referring to the distal side of a device or part of a device, the referral is to the side facing away from the skin, when the ostomy appliance is worn by a user. In other words, the proximal side is the side closest to the user, when the appliance is fitted on a user and the distal side is the opposite side—the side furthest away from the user in use.

The axial direction, or axially, is defined as the direction of the stoma when the appliance is worn by a user. Thus the axial direction is substantially perpendicular to the abdominal surface of the user.

The radial direction, or radially, is defined as transverse to the axial direction that is transversely to the direction of the stoma.

An "adaptable ostomy base plate" is intended to define that at least a part of the ostomy base plate can change its form or shape by an intended interaction of a user or health care professional.

A "flexible top film" is intended to define a film material carrying or having disposed thereon, adhesive material to make the product adhere to the skin of a user and that the top film material does not break or become weaker even at very high elongation or stretching rates. A flexible top film is further defined below.

An "elastic skin-friendly adhesive" is intended to define an adhesive material having a low risk of irritating the skin of a user and that the adhesive material is capable of following the elongations and relaxations of the flexible top film without breaking or substantially changing characteristics. An elastic skin-friendly adhesive is further defined below.

A "substantially convex shape" is intended to define that an element or its corresponding surface has a shape or form that provides an overall convexity. In other words, while a smaller section or zone making up part of the overall element or its corresponding surface may have e.g. a linear shape or form, the element or surface as a whole has a convex shape. It is of course to be understood that if for a sheet- or plate-like element one major surface has a convex shape, the opposite major surface may necessarily have a corresponding concave shape. However, for clarification purposes only, and in relation to the present application, "convex" may preferably refer to the proximal side and "concave" to the distal side as both defined above.

Similarly, a "substantially concave shape" is intended to define that an element or its corresponding surface has a shape or form that provides an overall concavity.

"Initial engagement" is intended to define the first contact between the ostomy base plate and the skin surface of the user in the process of applying the product; however not meaning that the ostomy base plate is fully and functionally correct attached to the skin surface.

"Permanent engagement" is intended to define the engagement or attachment of the ostomy base plate when the application process is completed and the ostomy base plate is fully and functionally correct attached to the skin surface. However, it should be understood that permanent engagement is only intended to mean for the normal life- or wear time of the ostomy base plate.

"Release liner" is intended to define a liner covering the proximal (skin contacting) side of the skin-friendly adhesive that ensures at least that the properties of the adhesive are preserved and that the adhesive surface is not laid open until just before the use.

"Fittingly engage" is intended to define that the attachment between the ostomy base plate and the skin surface is as good as possibly feasible and at least with no or only insignificant creases or folds on the proximal surface of the base plate.

"Peristomal skin surface" is intended to define an area of the skin surface adjacent to and surrounding the stoma. The extent of the area may be considered to correspond approximately to a skin surface area covered by at least a first section of the ostomy base plate—the first section then being closer to the stoma than a second section.

"Invertible" is intended to define that the at least first and/or second section provides little or no resistance to being shifted from a substantially convex shape to a substantially concave shape, or vice versa, by a movement involving no sudden switching or "flipping-over" of the section (i.e. as it is known from a bi-stable construction which may change shape when a certain force-threshold is reached).

In a first aspect, the invention relates to an adaptable ostomy base plate comprising a flexible top film and having at least a first and a second section, at least a first elastic skin-friendly adhesive on a proximal surface of said flexible top film, a stoma-receiving through-going hole in said first section, said first section being adjacent to and extending radially from said through-going hole and said second section surrounding said first section, and one or more release liners, wherein at least said first section has a first substantially convex shape for initial engagement with a peristomal skin surface, at least said first section being invertible to a first substantially concave shape to fittingly engage said first section to a topography of the peristomal skin surface for permanent engagement thereto.

By the invention according to the first aspect, a number of advantageous effects are achieved. First of all, a user having a stoma located on a bulge or hernia, or on an otherwise "hilly" topographic skin surface, has improved control of the product application procedure.

This effect is at least partly achieved in the following manner: subsequent to removal of at least one release liner covering at least partly the first section, the user engages a part of the first section immediately adjacent the stoma-receiving through-going hole with the peristomal skin surface, whereby only a small area of the adhesive on the proximal surface of the flexible top film is engaged with the peristomal skin surface.

Thereby, the user is provided with the opportunity to correct the positioning of the ostomy base plate to a more suitable position in case of misalignment of the initial engagement without having engaged the whole of the proximal adhesive surface of the flexible top film with the skin surface. This may be particularly advantageous in cases where the user has limited or no visual contact with the stoma.

Furthermore, since at least the first section has a first substantially convex shape, a user reaching down to the stoma located on the bulge or hernia in order to apply the product will have improved tactile and/or visual contact with the stoma and/or the peristomal area. This is because the part of the first section not initially engaging the peristomal skin surface extends away from the skin surface, thus leaving some space between the base plate and the skin giving room for one or more of the user's fingers, and thereby the first section also does not block or impede possible visual contact for correct positioning of the base plate in relation to the stoma.

Once the initial engagement of the first section is effected, the invertible first section is inverted by the user to a first substantially concave shape so as to fittingly engage the first section with the peristomal skin surface on the bulge or hernia.

It is important to understand the manner in which this is done. Due to the flexibility of the flexible top film and the elasticity of the skin-friendly adhesive, the adhesive proximal side of the first section will adapt smoothly to the topography of the peristomal skin surface when the user applies a gentle pressure to the distal surface of the first section.

This may advantageously, but not exclusively, be done by the user letting his finger or fingers describe one or more radial motions by placing the finger(s) immediately adjacent the stoma, providing pressure to the distal surface, and sliding the finger gently across the distal surface of the first section radially away from the stoma. Alternatively, the adaptation may be done by a motion placing a finger immediately adjacent to the stoma, providing pressure to the distal surface, and sliding the finger gently in a "spiral-like" pattern gradually away from the stoma over the whole distal surface of the first section.

However, regardless of the way of adaptation, at least the flexibility of the flexible top film and the elasticity of the skin-friendly adhesive along with the first substantially convex shape of the first section make the fitting engagement of the first section possible.

As can be understood from the above, the flexible top film and the elastic skin-friendly adhesive facilitate the inversion of the first section for application to the peristomal skin surface by a continuous, regular movement (or movements). This provides a user with improved control of the application procedure. This should be seen in contrast to a sudden movement which would be the case e.g. in the case of a bi-stable construction, i.e. a construction having one predetermined position where it changes shape from one form to another, e.g. from convex to concave.

The flexible top film according to the invention may be a blown film primarily based on one or more Ethylene Vinyl Acetate (EVA) materials, one or more thermoplastic polyurethane elastomeric (TPU) based materials and one or more polyethylene (PE) materials. Particularly, but not exclusively, the EVA and TPU based materials may provide a good basis for engagement of the top film with other elements of the ostomy base plate such as the adhesive(s) and optional first coupling means, or in the case of the base plate being used for a one-piece ostomy appliance, with the material of the collecting bag for human body wastes. The PE material(s) may particularly, but not exclusively, provide a suitable basis for shaping the flexible top film into a convex or concave shape to be able to fittingly engage with a topography of a user's skin surface.

In embodiments, the flexible top film is a three-layer laminate.

Particularly, but not exclusively, the flexible top film may be made as a laminate comprising three individual (blown) layers each of which is made from either EVA, TPU or PE or from a blend of these. In the three-layer laminate, the distal-most (with reference to the use situation of the ostomy base plate) layer may be made from a blend of Elvax® 3190, an EVA material from DuPont, and Orevac® 18360, a PE material from Arkema; the middle layer may be made from a blend of Elvax® 3190, Elastollan® 890, a TPU-Polyester material from BASF and Elastollan® 978, another TPU-Polyester material from BASF and; the proximal layer may also be made from a blend of Elvax® 3190, Elastollan® 890 and Elastollan® 978. In addition to these components each of the distal and proximal layers of the three-layer laminate may also comprise a minor amount of slip agent (to assist when unrolling the top film material for production of the ostomy base plate). The slip agent may be a PE/EVA polymer carrier containing silica, oleamid (fatty acid oleic acid) and erucamide (monounsaturated omega-9 fatty acid), such as Polystatic® 90200-2. The silica and the ole-/erucamides in the slip agent provide the slipping effect.

The overall thickness of the flexible top film may be in a range of 30-70µ, such as 35-50µ, such as approximately 40µ. In embodiments of the three-layer laminate, each individual layer may have a thickness of at least 10µ for ease of production of the individual layers.

The flexible top film may be stretched prior to being used in the production of the ostomy base plate. This will provide a pre-tensioning or bias in the flexible top film. The flexible top film may be stretched radially in all directions to obtain the same bias in all directions of the plane thereof. This pre-tensioning or bias in the flexible top film incurs additional flexibility to the flexible top film. Particularly, it may improve the film's ability to adapt to a certain shape in a shaping process.

The flexible top film may have a flexibility measured as a percentage of elongation of the flexible top film material before it fails (considered as the point where plastic deformation of the flexible top film occurs). The flexible top film may be 250-700% elongatable, such as 300-600% elongatable, such as 350-450% elongatable, such as 400% elongatable before failure.

The first elastic skin-friendly adhesive according to the invention may be a pressure sensitive adhesive composition suitable for medical purposes comprising a rubbery elastomeric base and one or more water soluble or water swellable hydrocolloids, the adhesive composition comprising a substantially homogeneous mixture of 25-60% of one or more polyisobutylenes, 3-35% of one or more styrene copolymers, and 20-60% of one or more hydrocolloids, wherein the percentage by weight of one or more polyisobutylenes and one or more styrene copolymers and one or more hydrocolloids add up to 100% by weight of the adhesive composition. For further information on such compositions reference is made to applicant's granted European patent EP1541180B1.

The thickness of the first elastic skin-friendly adhesive layer may be in a range of 1-2 mm, corresponding to 1000µ-2000µ, such as 1200µ-1800µ, such as 1400µ-1600µ.

For the production of the ostomy base plate, the following is an example of manufacture: first the adhesive(s) is/are provided on the proximal surface of the flexible top film and thereafter the at least one release liner is provided on the adhesive surface. At least the first section of the planar laminate blank is then subsequently placed in a vacuum-forming machine, the moulding tool having the relevant convex form. Heating means, such as a radiant heat source is placed in connection with the vacuum-forming machine in order to soften the laminate blank, and the laminate blank is subjected to heat and vacuum forming for an adequate holding time. Alternatively, the laminate blank may also be manufactured by means of a heat and pressure die or indeed any other suitable procedure.

In embodiments where the second section of the ostomy base plate is also convex shaped (or concave shaped) the moulding tool used in the process described above may be configured to provide both convex shapes (or convex shape of the first section and concave shape of the second section). Alternatively, the shaping process may be divided into more steps, e.g. first shaping the first section and separately shaping the second section. The stoma-receiving through-going hole may be cut in the ostomy base plate before or after the shaping process.

Due to its elasticity, the first skin-friendly adhesive may easily adapt to the convex shape of at least the first section together with the flexible top film and the at least one release liner in the shaping process. Indeed, subjected to the above described shaping process, at least the first section of the ostomy base plate according to the invention initially always has the convex shape notwithstanding its high degree of adaptability. As mentioned, this may be seen in contrast to e.g. the known bi-stable convex ostomy products that are relatively rigid and only adaptable in an "either inverted/not inverted" sense.

The at least one release liner used in connection with the ostomy base plate according to the invention, may suitably be a siliconised or fluorinated liner, such as a siliconised or fluorinated craft paper, polyethylene, polypropylene or polyethylene terephthalate film.

In embodiments, the second section has a second substantially convex shape being invertible to a second substantially concave shape.

This may be particularly advantageous to further improve the tactile and/or visual contact with the stoma and/or the peristomal area. In such embodiments, where then both the first and the second sections initially extend away from the skin surface, there will be additional space between the base plate and the skin giving plenty of room for the user's manual handling of the base plate during application. Also, thereby the second section does not block or impede the user's visual contact with the stoma.

The second section may be inverted and permanently engaged to the skin surface of the user in the same or substantially similar manner as the first section and as described above. The engagement of the second section to the skin surface is generally carried out after the first section has been permanently engaged with the peristomal skin surface. However, in the case of a two-piece ostomy appliance, it may be advantageous to engage the second section to the skin surface of the user only after the collecting bag has been coupled to correct engagement with the ostomy base plate.

The second section surrounds the first section of the adaptable ostomy base plate. In embodiments, a transition between the first and the second section may be defined by a zone where the two convex sections meet at an angle to each other.

This may be particularly, but not exclusively, advantageous if easy distinction of the sections by the user is required, e.g. facilitating the user's following of instructions for use.

In other embodiments, the transition may be straight or smooth (i.e. no angle between the sections) thus ruling out at least any visual difference between the sections. If the first and second sections are arranged according to such embodiments there may be no difference between the convexity of the first and second section, thus the first and second section may be perceived, or actually manufactured, as a single "coherent" or integral convex section. This may be particularly relevant in relation to minimizing production costs.

Additionally, however, the first and the second section may have different convexities. This could by way of example be relevant in relation to different dimensions and/or sizes of the ostomy base plate.

In embodiments, the second section has a second substantially concave shape. This should be seen in contrast to the embodiments described above wherein the second section is invertible to a second substantially concave shape. Therefore, in these embodiments the second section has a pre-defined substantially concave shape. A transition between the first and second section is defined by a zone where the two sections meet at an angle to each other. Consequently, the initial substantially convex shape of the first section makes the first section extend away from the skin surface, while the substantially concave shape of the second section makes the second section extend toward the skin surface from the position of the transition between the sections.

This may be particularly, but not exclusively, advantageous where the adaptable ostomy base plate according to the invention is used in a two-piece ostomy appliance with adhesive-type coupling means. In such two-piece appliances a planar coupling flange is typically attached to the distal side of the base plate and receives mating (pressure-sensitive adhesive) coupling means attached around the opening of a collecting bag for human bodily wastes. Optimization of the coupling effect of these adhesive-type coupling means requires that the user is capable of applying the necessary pressure to properly engage the adhesive. In this regard, it is particularly advantageous if the user can apply pressure to a distal side of the coupling (e.g. with his index finger), while simultaneously holding against the proximal side of the coupling (e.g. with his thumb). Therefore, as the concave shape of the second section according to these embodiments of the invention enables more space between the proximal side of the planar coupling flange and the distal side of the second section, the user can more easily apply e.g. his thumb in that space which effectively improves the coupling procedure.

In embodiments, the ostomy base plate according to the invention further comprises a substantially planar surface zone between said first and second sections.

"Substantially planar" is intended to define that a surface zone of the ostomy base plate has a linear or planar form close to parallel with a straight horizontal line; at least it is not inclined in relation to such horizontal line by more than +/−10 degrees. At least this definition is meant to clearly identify that the surface zone does not possess any kind of convex or concave shape in contrast to the first and second section.

The substantially planar surface zone between the sections may provide extra control with regard to the user's handling of the product in the application procedure and may further hinder that the first and/or the second sections become obstructive in e.g. the distal or proximal direction with regard to e.g. the user's clothes or with regard to other objects or other physical areas of contact on the user's body. This may be particularly, but not exclusively, efficient, if a relatively large adhesive area of the ostomy base plate is needed (e.g. for high-volume output collecting bags).

The substantially planar surface zone may form at least part of a first transition between the first section and the zone and/or form at least part of a second transition between the second section and the zone.

In embodiments, the substantially planar surface zone distally accommodates first coupling means for coupling engagement with corresponding coupling means on a collecting bag for human body wastes.

The first coupling means may comprise an annular ring having a flange or similar member extending axially away from the planar surface zone to engage with engaging second coupling means on a collecting bag such as a corresponding annular ring with a channel for receiving the flange. Alternatively, the first coupling means may comprise a radially extending annular flange that provides a receiving surface for receipt of second coupling means on a collecting bag such as an annular adhesive flange. However, these are mere examples of typical coupling means for ostomy appliances; others types of engaging coupling means are not to be considered excluded.

The first coupling means may be attached to the substantially planar surface by welding, heat laminating, gluing or other commonly known suitable joining procedures. In some cases, the first coupling means need not be directly joined to the surface, but may instead be joined through means of an additional intermediate element, such as a film material element connected to the substantially planar surface at one end and to the first coupling means at another end.

By accommodating the first coupling means in the first substantially planar surface zone a user faced with applying the collecting bag to the base plate by engaging the first and second coupling means may be provided with the possibility of holding his thumb against the substantially planar surface zone proximally while applying pressure with his index finger on the distal side of the coupling means. This is advantageous for achieving a safer and more complete engagement of the coupling means thus leading to reduced risk of leakages. Furthermore, by accommodating the first coupling means on the substantially planar surface zone the joining of the first coupling means to the zone is easier and thus production costs are reduced.

In other embodiments, the first or second section distally comprises first coupling means for engagement with corresponding coupling means on a collecting bag for human body wastes.

In these embodiments, the first coupling means may be provided on either the first or the section. However, this does not rule out the presence of a possible substantially planar surface zone between the first and the second sections. Positioning the first coupling means on the first section may be particularly advantageous if the adhesive proximal surface of the ostomy base plate is relatively small e.g. lack of a suitable adhesive receiving skin surface due to additional physical conditions on the user's skin surface. A position of the first coupling means on the second section may e.g. be advantageous in the case of a large diameter stoma situated on a relatively small bulge or hernia.

In embodiments, the adaptable ostomy base plate comprises a second skin-friendly adhesive on the proximal surface of the flexible top film.

The second skin-friendly adhesive may be provided so as to give the proximal surface of the base plate different characteristics and/or effects. As an example, the second skin-friendly adhesive may comprise smaller or a larger amount of a moisture absorbing component such as hydrocolloids and/or be more or less adaptable than the first skin-friendly adhesive. The second skin-friendly adhesive may be provided in a single or in multiple zones or areas. The zones or areas may have particular suitable shapes or forms depending on the function or effect of the second skin-friendly adhesive.

In embodiments, the first elastic skin-friendly adhesive is provided on the first section and the second skin-friendly adhesive is provided on the second section.

This disposition of the first and second skin-friendly adhesive effectively provides an ostomy base plate wherein the first skin-friendly adhesive having one set of characteristics covers the peristomal area, and the second skin-friendly adhesive having another set of characteristics covers the skin surface around (radially beyond) the peristomal skin surface.

In embodiments, the second skin-friendly adhesive is elastic. This means, that in addition to the first elastic skin-friendly adhesive, also the second skin-friendly adhesive has elastic properties. The second skin-friendly adhesive may be more or may be less elastic than the first elastic skin-friendly adhesive or the two adhesives may even have identical elasticities if desired.

Where the elasticity of a construction is typically measured by the tensile elasticity Modulus (E) (also known as Young's Modulus) the elasticity of an adhesive is typically measured by the shear Modulus (G).

The shear Modulus of a viscoelastic material like an adhesive can be divided into a viscous part called the Loss Modulus (G") and an elastic part called the Storage Modulus (G'). The elastic response of the adhesives can therefore be measured by measuring G' by dynamic mechanical analysis (DMA), which is a well-known and established procedure to a skilled person working in the field of adhesives.

Body movements according to normal daily life routines typically occur at frequencies around 1-10 Hz. At these frequencies, the G' of the first elastic skin-friendly adhesive may be in a range from 850-1200 MPa, whereas G' of the second elastic skin-friendly adhesive may be in a range from 40-80 MPa.

In embodiments, the second elastic skin-friendly adhesive comprises a polar plasticising oil or a combination of polar plasticising oils in the content of above 10% (w/w) of the final second adhesive, and at least one polar polyethylene copolymer, wherein the content of the polyethylene copolymer is 10-50% (w/w) of the final second adhesive, the polyethylene copolymer has a melt flow index below 2 g/10 min (190° C./21.1N).

Polymers that may be used for the second skin-friendly adhesive will generally be copolymers of ethylene and a polar monomer. The copolymers typically comprise less than about 70% ethylene, have water vapour transmission of more than 50 g/m$^2$/day and a melt flow index of less than 2 g/10 min (190° C./21.1N). The melt flow index can be measured by the methods given in ISO 1133 and ASTM D1238. Examples of such polymers are copolymers of ethylene and vinyl acetate and copolymers of ethylene and butyl acrylate. Particularly preferred is ethylene and vinyl acetate copolymers with more than about 40% (w/w) vinyl acetate, a melt flow index of less than 2 g/10 min (190° C./21.1N), and a water vapour transmission of more than 50 g/m$^2$/day for a 150 μm sheet when measured according to MVTR Test Method (inverted cup method).

Polar oils, which may be used in the invention, will generally be those that have good sol-ubility in the polar domains of the polymer, i.e. provide softness without sacrificing too much tensile strength of the polymer. Oils that can support good water vapour permeabil-ity are preferred. Examples of such oils are vegetable and animal oils and derivatives thereof. Preferred polar oils are esters, ethers and glycols and particularly preferred is Poly Propylene Oxide, e.g. alpha-butoxy-polyoxypropylene.

Further information on the types of adhesives suitable for the second skin-friendly adhesive disclosed in these embodiments is available in applicant's published application WO 2009/006901A1.

In embodiments, the thickness of the second elastic skin-friendly adhesive is 300-700μ, such as 550-650μ, such as 600μ.

Particularly, when using the above defined polyethylene copolymer based adhesive as the second elastic adhesive in the thickness of 300-700μ, a flexible and soft adhesive base plate which can be handled without a stiffening, or stabilizing, layer is achieved. For further information on the combination of such a thickness range and the defined polyethylene copolymer, reference is made to applicant's published application WO 2012/022352A1.

In embodiments, at least the second section further comprises a reinforcing element. Thereby, the second section may be easier to handle because it is at least partly stiffened or stabilized by the reinforcing element. Particularly in the case of a relatively large (diameter) ostomy base plate according to the invention this may help the user to control the product. By way of example, the reinforcing element could be a permeable or perforated film layer such as of a blown film but also including non-wovens or foamed film layers. The reinforcing element may be embedded in the second skin-friendly adhesive or located between the distal surface of the adhesive and the proximal surface of the flexible top film.

DETAILED DESCRIPTION OF THE DRAWING

Initially, it shall be noted that the figures are schematic illustrations intended only to address the principles and functions of the base plate according to the invention and are not to be considered limiting to the scope of the attached claims. Furthermore, the figures and particularly the individually illustrated elements are not necessarily to scale, neither individually nor in relation to each other.

FIG. 1a shows a schematic sectional view of an adaptable ostomy base plate 10 according to embodiments of the invention. The base plate has a first section 1 and a second section 2a and is further shown with an optional substantially planar surface zone 3 between the first 1 and second 2a sections. The first 1 and second 2a sections have a substantially convex shape. At first transition 5 between the first 1 and second 2a sections is also indicated. The ostomy base plate 10 comprises a flexible top film 8 having disposed thereon at least a first elastic skin-friendly adhesive 6. Up until use, the ostomy base plate 10 further comprises at least one release liner 9 (FIG. 6) on the at least first adhesive. The ostomy base plate 10 may optionally further comprise at least a second skin-friendly adhesive 7 (FIG. 1b) disposed on the flexible top film 8. A stoma-receiving through-going hole 4 is also illustrated. Finally, first coupling means 20 for engagement with second coupling means on a collecting bag for human body wastes.

Figure 1B:
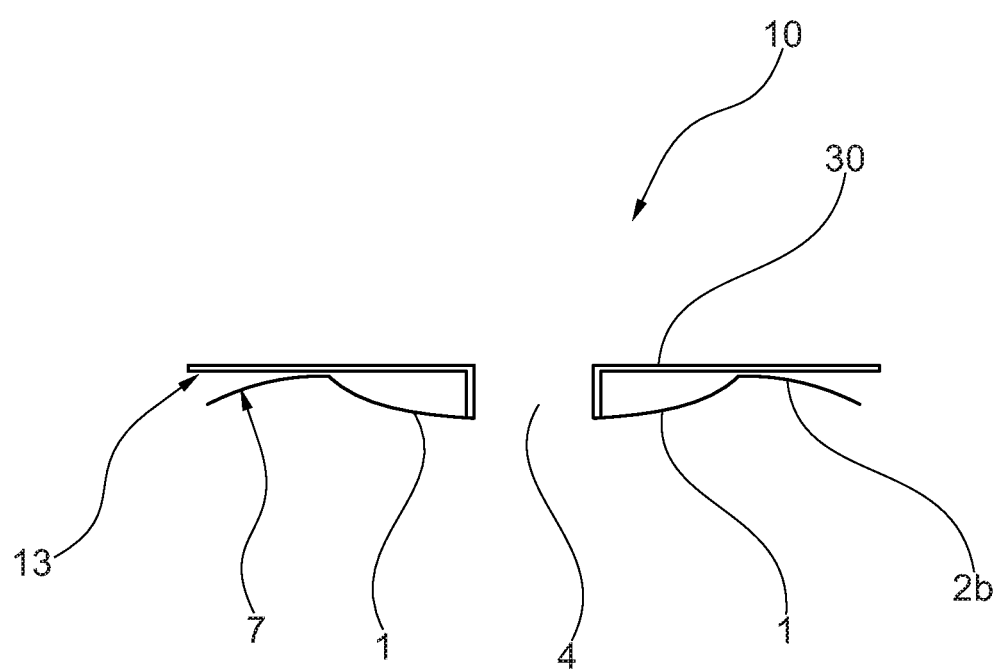
FIG. 1*b* is a schematic sectional view of an ostomy base plate according to other embodiments of the invention.

FIG. 1b also shows a schematic sectional view of an adaptable ostomy base plate 10 according to alternative embodiments of the invention. The base plate 10 has a convex shaped first section 1 and a concave shaped second section 2b. The configuration of the base plate 10 according to these embodiments are particularly useful when the first coupling means for engagement with second coupling means on a collecting bag for human body wastes is a planar flange 30, as shown in the figure. This provides space for a user to place a finger between the distal surface 11 (FIG. 2) of the ostomy base plate 10 and the proximal side 13 of the planar flange 30, so as to press the second coupling means on the collecting bag (such as an adhesive flange) securely onto the planar flange 30.

Figure 2:
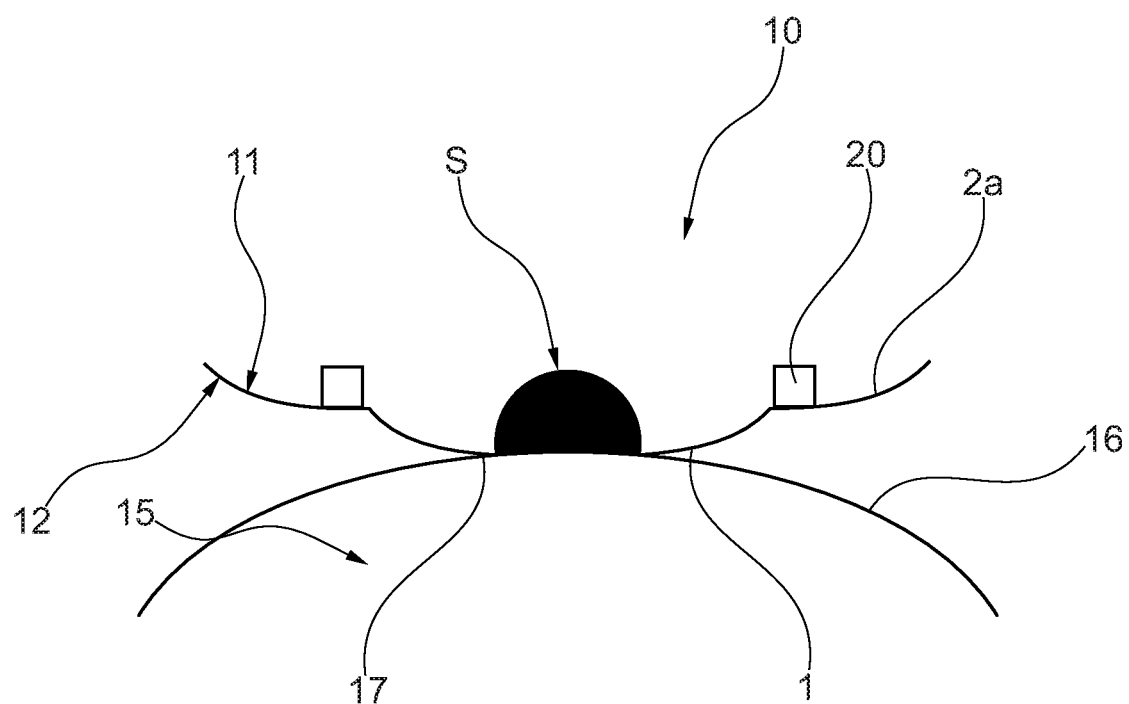
FIG. 2 is a schematic sectional view of an ostomy base plate according to embodiments of the invention placed on the skin surface of a user.

FIG. 2 is another schematic sectional view showing the ostomy base plate 10 in an initial position in the procedure of applying the base plate 10 to a user's skin surface 16. After removal of one or more release liners covering at least the first section 1, the first section 1 is brought into initial engagement with the peristomal skin surface 17 surrounding a stoma S. As can be understood from FIG. 2, the convex shape of the first 1 and second 2a sections of these embodiments keeps a majority of the proximal surface 12 of the base plate 10 out of contact with the skin surface 16, 17 which aids the user in the application procedure since focus need only be on the first section. Additionally, as it is initially only the innermost part of the first section 1 immediately adjacent to the stoma S that is in adhesive contact with the peristomal skin surface 17, the user is provided with a possibility of adjusting or correcting the position of the base plate 10 before applying a larger adhesive area. Furthermore the ostomy base plate 10 is shown in position on a bulge or hernia 15 on the user's skin surface 16. Due to the convex shape of at least the first section 1, the ostomy base plate 10 according to the invention is particularly suitable for users suffering from hernia.

Figure 3:
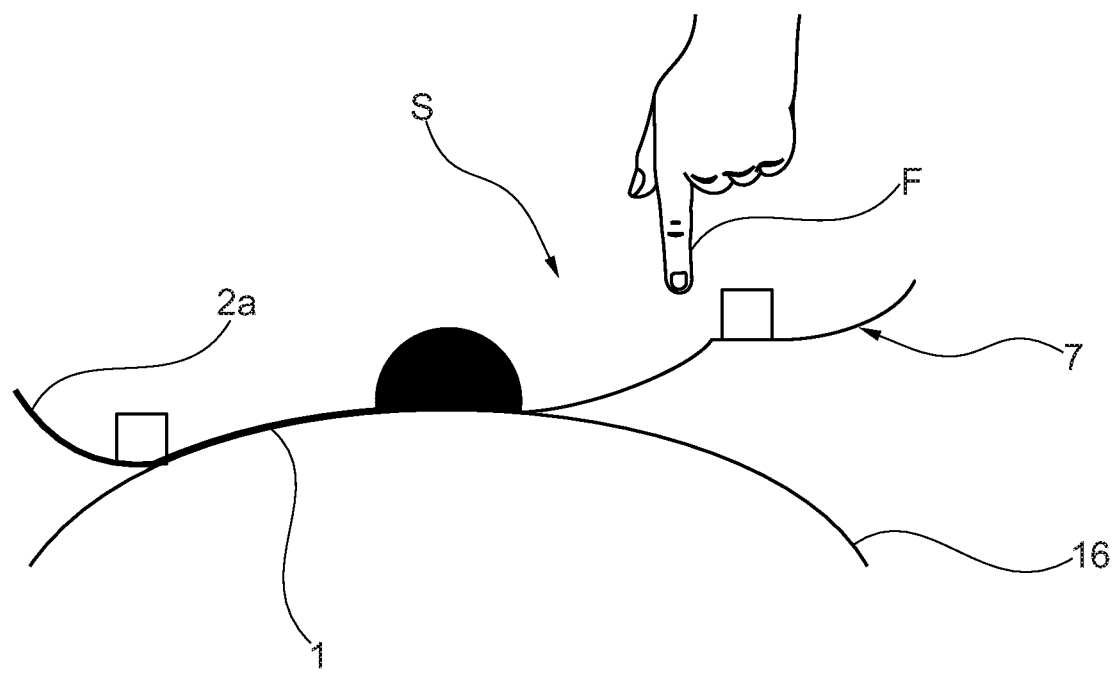
FIG. 3-5 are schematic sectionals view of an ostomy base plate according to the embodiments introduced in FIG. 2 shown in different steps of the application procedure.

FIG. 3 is another schematic sectional view showing the ostomy base plate 10 in a next step of the application procedure. Part of the first section 1 has been permanently engaged with the peristomal skin surface 17 (FIG. 2) by a user applying pressure to the distal surface 11 with one or more fingers F. A remaining part of the first section 1 and the second section 2a, both with substantially convex shape, have not yet been engaged with the skin surface 16. As indicated, at least the second section 2a may have disposed a second skin-friendly adhesive 7 thereon. Furthermore, although not shown in FIG. 3, the second section 2a may have at least one release liner (separate from release liner(s) on the first section 1) covering at least part of the second section 2a. As can be understood from FIG. 3 at least, in the application procedure it may be an advantage to keep release liner(s) on the second section 2a in place until the first section 1 has been fully, permanently engaged with the peristomal skin surface 17.

Figure 4:
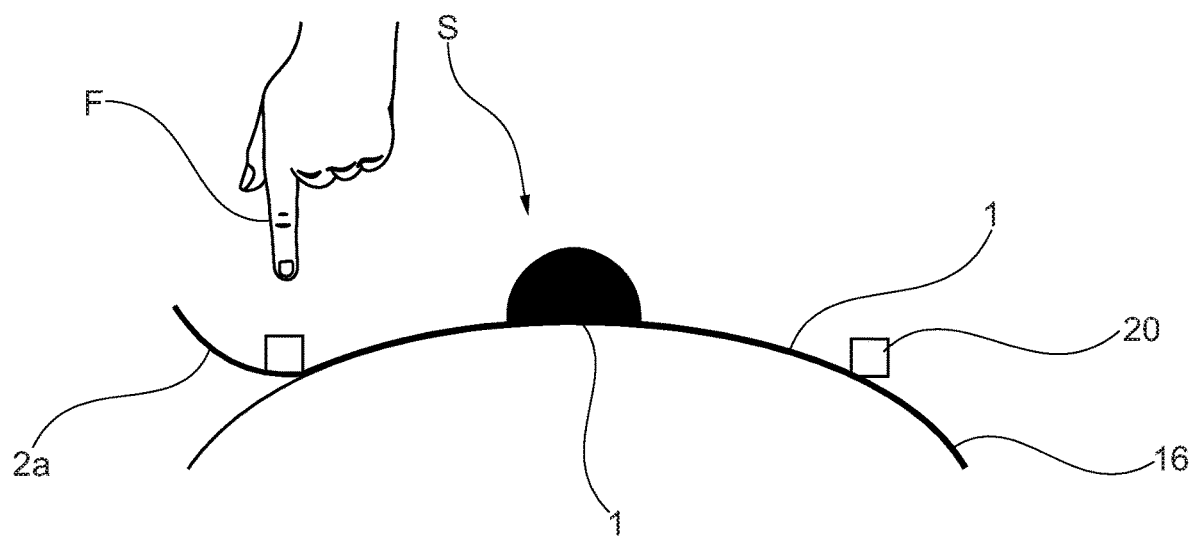

FIG. 4 is another schematic sectional view showing the ostomy base plate 10 in a next step of the application procedure. In this figure, only a last part of the second section 2a remains unengaged with the skin surface 16.

Figure 5:
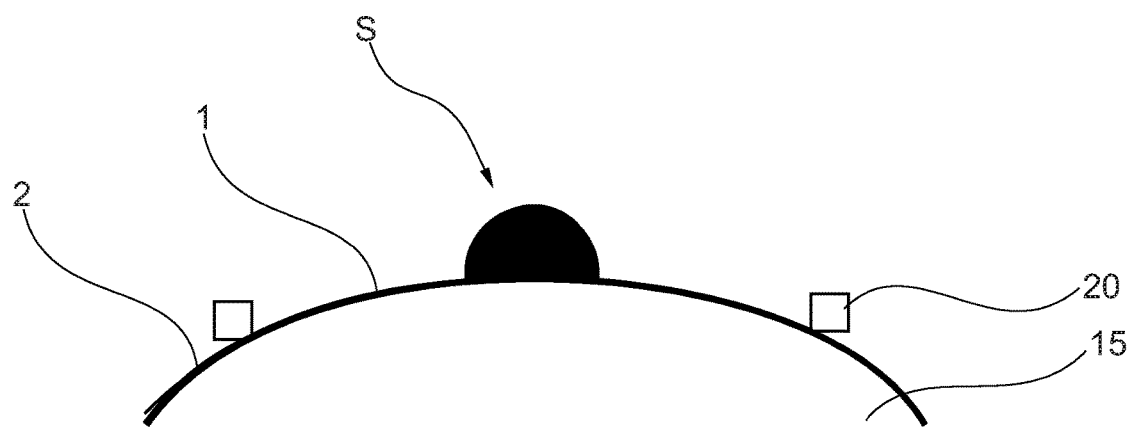

In FIG. 5, which again is another schematic sectional view showing the ostomy base plate 10 it is completely and correctly applied to the skin surface 16 of a user. Thus, the first section 1 is permanently engaged with the peristomal skin surface 17 and the second section 2 is permanently engaged with the surrounding skin surface 16. As can be seen from FIG. 5, the adaptable ostomy base plate 10 according to the invention thus fittingly engages the skin surface on the bulge or hernia 15. The shown (optional) first coupling means 20 are ready for engagement with corresponding second coupling means on a collecting bag in the case of a two-piece implementation of the invention.

Figure 6:
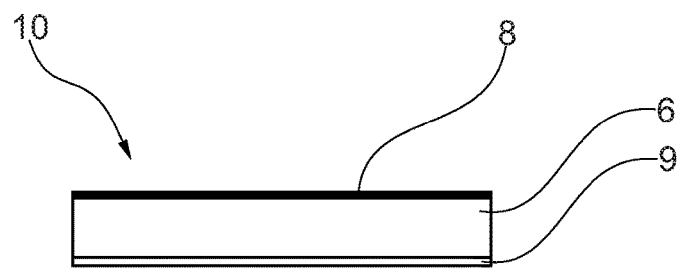
FIG. 6 is a schematic simplified sectional view of the a base plate configuration according to embodiments of the invention.

FIG. 6 is a simple schematic sectional view of a cut-out of the adaptable ostomy base plate 10. The cut-out is not shown with a convex shape, but it is to be understood that this could evenly be the case depending on the width of the cut-out considered. The base plate 10 has a flexible top film 8, a skin-friendly adhesive layer 6 and a release liner 9. The relative thicknesses between the different layers are only shown to differentiate the layers from each other and shall not be considered an actual display of any relational thicknesses.

Figure 7:
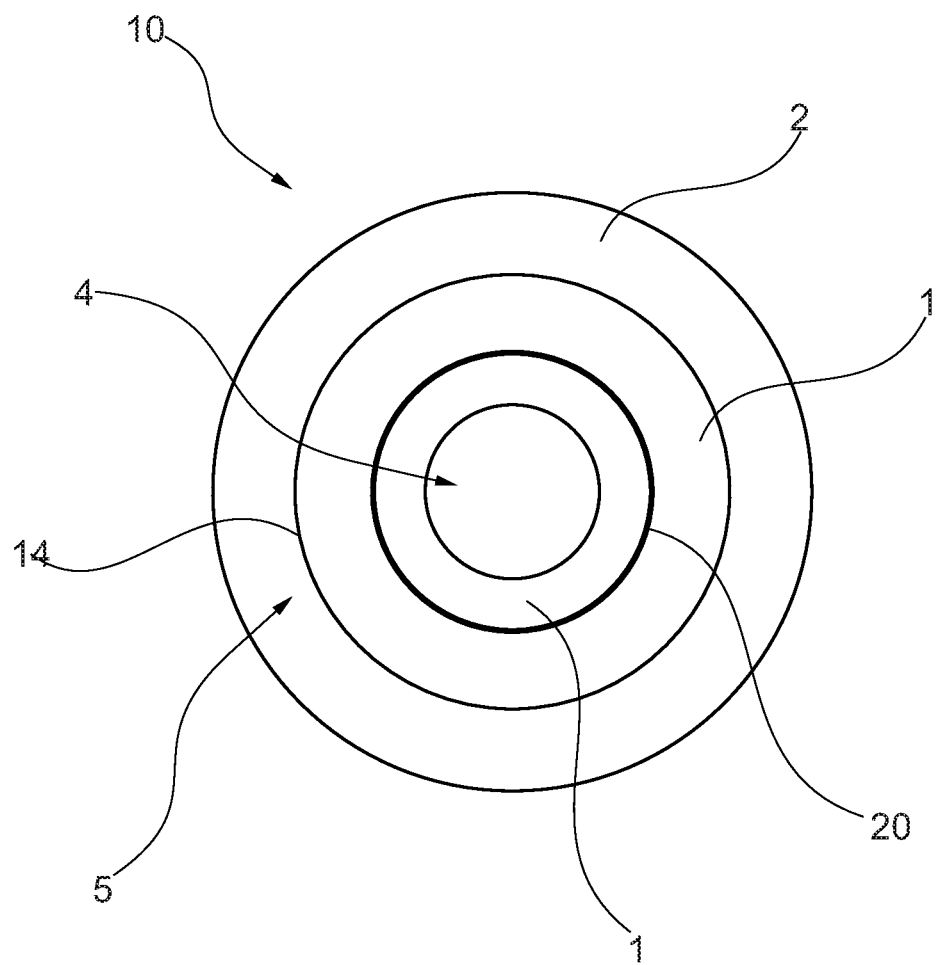
FIG. 7 is a schematic planar top view of a distal surface of an adaptable ostomy base plate according to embodiments of the invention.

FIG. 7 is a schematic planar top view of the distal surface 11 of the adaptable ostomy base plate 10. The base plate 10 is shown with a circular configuration but may also be applied with an oval or elliptical configuration. Illustrated are a second section 2 and a first section 1. The first section 1 is shown hosting first coupling means 20 in the form of an annular ring for engagement with corresponding coupling means on a collecting bag (not shown). A transition 5 between the first 1 and second section 2 is shown highlighted by circular line 14, however the transition 5 is not necessarily visible in reality, at least not on the distal surface 11 of the base plate 10.

Example

In a particular example of the adaptable ostomy base plate according to the invention, which may be further understood by consulting the drawing, particularly FIGS. 6 & 7, the following materials, dimensions and process parameters are applied:

The flexible top film is a non-stretched, three-layer laminate wherein the distal-most layer is a blend of Elvax® 3190 and Orevac® 18360; the middle layer is a blend of Elvax® 3190, Elastollan® 890 and Elastollan® 978; the proximal layer is a blend of Elvax® 3190, Elastollan® 890 and Elastollan® 978. The distal and proximal layers additionally comprise a minor amount of slip agent according to the invention. The thickness of the flexible top film is 40μ.

A first elastic skin-friendly adhesive according to the invention is provided on the proximal surface of the flexible top film in an area or zone corresponding to the first section of the base plate (numeral 1 in FIG. 7). The thickness of the first elastic skin-friendly adhesive is approximately 1600μ (subject to negligible production variations).

A second skin-friendly adhesive is chosen as an elastic skin-friendly adhesive according to embodiments of the invention, and is provided on the proximal surface of the flexible top film in an area or zone corresponding to the second section of the base plate (numeral 2 in FIG. 7). The second section annularly surrounds the first section of the base plate. The thickness of the second elastic skin-friendly adhesive is approximately 600μ (subject to neglicable production variations).

A single release liner according to the invention is provided on the proximal adhesive surface of the base plate. The release liner has a thickness of 80μ.

In the example, both the first and the second section have a substantially convex shape. To obtain the substantially convex shapes, an ostomy base plate blank (flexible top film+adhesives+release liner) as defined in this example is pre-heated at 150° C. for 28 seconds and then formed in a vacuum-forming machine with a moulding tool provided with two respectively convex sections. The depth of the convexities in the moulding tool is 12 mm. A pre-defined stoma receiving through-going hole (size e.g. Ø25 mm) is punched in the ostomy base plate blank after the vacuum-forming.

In the example, the ostomy base plate has a circular configuration with an overall diameter of Ø100 mm. The base plate allows the user the opportunity to adapt the pre-defined stoma receiving through-going hole to fit the size and shape of his individual stoma up to a maximum diameter of Ø53 mm (in FIG. 7 this may be considered illustrated by numeral 4).

The second section 2 of the base plate 10 annularly surrounding the first section (see FIG. 7), is at least 10 mm wide. Furthermore, in the example (and as schematically illustrated in FIG. 7) the first section 1 extends at least 10 mm radially beyond a radially outer periphery of the first coupling means in the form of annular ring 20. The portion of the first section 1 extending radially inward of the first coupling means 20 depends on the size of the user-adapted stoma receiving hole 4 as described above.

The invention claimed is:

1. An ostomy appliance comprising a base plate, the base plate comprising:
    a film including a distal surface opposite from a proximal surface;
    an annular ring connected to the distal surface of the film and adapted to couple with a waste collection bag;
    an adhesive disposed on the proximal surface of the film;
    a release liner removably attached to the adhesive; and
    a stoma-receiving through-going hole formed through the film and the adhesive and the release liner at a location inside of the annular ring, with a first section of the base plate extending radially from the stoma-receiving through-going hole to a second section of the base plate, and the second section extending radially from the first section to an outermost perimeter edge of the base plate;
    wherein the base plate is formed to have a heat-set curvature such that a proximal side of the second section is convex when the base plate is viewed from a proximal direction and a distal side of the second section is concave when the base plate is viewed from a distal direction,
    wherein the base plate is invertible away from the heat-set curvature to provide the proximal side of both the first section and the second section with a concave curvature when the base plate is viewed from the proximal direction.

2. The base plate of claim 1, wherein the base plate is invertible away from the heat-set curvature to provide the proximal side of the second section with a concave curvature when the base oate is viewed from the proximal direction and to provide the distal side of the second section with a convex curvature when the base plate is viewed from the distal direction.

3. The base plate of claim 1, wherein the base plate is invertible away from the heat-set curvature to first provide the proximal side of the first section with a first concave curvature and to subsequently provide the proximal side of second section with a second concave curvature when the base plate is viewed from the proximal direction.

4. The base plate of claim 1, wherein the annular ring includes a planar attachment surface connected to the distal surface of the film and a flange extending in an axial direction away from the planar attachment surface.

5. The base plate of claim 1, wherein the ostomy appliance further comprises an ostomy waste bag connected to the annular ring.

6. The base plate of claim 1, wherein the adhesive comprises a first adhesive disposed on the proximal surface of the film along the first section of the base plate and a second adhesive disposed on the proximal surface of the film along the second section of the base plate, with the second adhesive different from the first adhesive.

7. The base plate of claim 1, wherein the adhesive is elastic.

8. The base plate of claim 1, wherein the adhesive comprises a first adhesive disposed on the proximal surface of the film along the first section of the base plate and a second adhesive disposed on the proximal surface of the film along the second section of the base plate, and the second adhesive comprises a polar plasticizing oil or a combination of polar plasticizing oils having a content of above 10% (w/w) of the final second adhesive.

9. The base plate of claim 1, wherein the adhesive comprises a first adhesive disposed on the proximal surface of the film along the first section of the base plate and a second adhesive disposed on the proximal surface of the film along the second section of the base plate, and the second adhesive comprises at least one polar polyethylene copolymer, wherein a content of the polyethylene copolymer is 10-50% (w/w) of the final second adhesive.

10. The base plate of claim 9, wherein the polyethylene copolymer has a melt flow index below 190° C./21.1N.

11. The base plate of claim 1, wherein the adhesive comprises a first adhesive disposed on the proximal surface of the film along the first section of the base plate and a second adhesive disposed on the proximal surface of the film along the second section of the base plate, and a thickness of the first adhesive is approximately 1600 micrometers and a thickness of the second adhesive is approximately 600 micrometers.

12. The base plate of claim 1, wherein the second section of the base plate comprises a reinforcing element.

13. The base plate of claim 1, wherein the film is a three-layer laminate.

14. The base plate of claim 1, wherein the film is adapted to elongate in a range from 400% to 700% before failure.

15. The base plate of claim 1, wherein the outermost perimeter edge of the base plate is circular.

16. The base plate of claim 1, wherein the outermost perimeter edge of the base plate is elliptical.

* * * * *